United States Patent
Igney et al.

(10) Patent No.: US 9,814,432 B2
(45) Date of Patent: Nov. 14, 2017

(54) DEVICE AND METHOD FOR ASSISTING THE ALIGNING OF A DOCKABLE PATIENT SUPPORT

(71) Applicants: Claudia Igney, Erlangen (DE); Markus Petsch, Erlangen (DE)

(72) Inventors: Claudia Igney, Erlangen (DE); Markus Petsch, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/959,099

(22) Filed: Dec. 4, 2015

(65) Prior Publication Data
US 2016/0166216 A1    Jun. 16, 2016

(30) Foreign Application Priority Data
Dec. 11, 2014    (DE) .......................... 10 2014 225 519

(51) Int. Cl.
*G01B 11/26*    (2006.01)
*A61B 6/04*    (2006.01)
(Continued)

(52) U.S. Cl.
CPC .......... *A61B 6/0407* (2013.01); *A61B 5/0555* (2013.01); *A61B 5/704* (2013.01)

(58) Field of Classification Search
CPC ... A61B 6/0407; A61B 5/0555; A61B 6/0457; A61B 6/04; A61B 6/0421; A61B 6/547;
(Continued)

(56) References Cited

U.S. PATENT DOCUMENTS

RE29,025 E  *  11/1976  Hansen ................ B65G 1/0421
                                                    356/138
5,142,559 A  *  8/1992  Wielopolski ............ A61B 6/08
                                                    250/492.3
(Continued)

FOREIGN PATENT DOCUMENTS

CH    WO 2007062788 A1  *  6/2007  ........... A61G 1/0293
DE    112013005667 T5      9/2015
(Continued)

OTHER PUBLICATIONS

Espacenet English translation of the EP document: EP 1854506.*
(Continued)

*Primary Examiner* — Tarifur Chowdhury
*Assistant Examiner* — Mohamed K Amara
(74) *Attorney, Agent, or Firm* — Lempia Summerfield Katz LLC

(57) ABSTRACT

A device for assisting the aligning of a patient support dockable onto an operating table is provided A sensing unit is configured to be arranged on the patient support or the operating table and configured to sense a feature of the patient support and/or of the operating table, said feature lying opposite the sensing unit. The sensing unit configured to sense a position-dependent physical interaction and herefrom to generate a signal that depends on the spatial relative position between the patient support and the operating table. An evaluating unit is configured to receive the signal from the sensing unit and to generate an output that characterizes the relative position between the operating table and the patient support.

19 Claims, 7 Drawing Sheets

(51) Int. Cl.
*A61B 5/055* (2006.01)
*A61B 5/00* (2006.01)

(58) Field of Classification Search
CPC ....... G01B 11/26; G01B 11/14; G01B 11/002; G01B 11/00; G01B 11/27; G01B 11/026
See application file for complete search history.

(56) References Cited

U.S. PATENT DOCUMENTS

| | | | |
|---|---|---|---|
| 8,442,617 B2 * | 5/2013 | Scarth | A61B 5/0555 378/63 |
| 2002/0161294 A1 * | 10/2002 | Drobnitzky | A61B 5/0555 600/410 |
| 2004/0057557 A1 * | 3/2004 | Nafstadius | A61B 6/04 378/209 |
| 2005/0080333 A1 * | 4/2005 | Piron | A61B 8/0825 600/417 |
| 2007/0238950 A1 * | 10/2007 | Vija | A61B 6/032 600/407 |
| 2008/0210853 A1 | 9/2008 | Gunzert-Marx et al. | |
| 2010/0031443 A1 * | 2/2010 | Georgiev | A61B 5/0555 5/601 |
| 2011/0154569 A1 * | 6/2011 | Wiggers | A61B 6/0407 5/81.1 R |
| 2012/0049084 A1 * | 3/2012 | Abenaim | A61B 6/0407 250/454.11 |
| 2012/0136196 A1 * | 5/2012 | Foxall | A61B 5/055 600/21 |
| 2013/0342350 A1 * | 12/2013 | Popescu | G08B 21/02 340/573.1 |
| 2014/0046212 A1 * | 2/2014 | Deutschmann | A61B 6/03 600/567 |
| 2014/0080413 A1 * | 3/2014 | Hayes | H04B 5/0037 455/41.1 |
| 2014/0155728 A1 * | 6/2014 | Lee | A61B 6/462 600/407 |
| 2015/0320382 A1 | 11/2015 | Martinez Ferreira et al. | |
| 2016/0296185 A1 * | 10/2016 | Gemmel | A61B 6/4441 |

FOREIGN PATENT DOCUMENTS

| | | | | |
|---|---|---|---|---|
| EP | 1854506 A1 | | 11/2007 | |
| IT | WO 2008104522 A2 | * | 9/2008 | ........... A61B 5/0555 |
| JP | 2002325763 A | * | 11/2002 | ........... A61B 5/0555 |
| JP | WO 2007043329 A1 | * | 4/2007 | ........... A61B 6/4494 |
| JP | 2013248402 A | * | 12/2013 | ............ G01B 11/24 |
| NL | WO 2015063191 A1 | * | 5/2015 | ............. A61B 6/027 |

OTHER PUBLICATIONS

"MAGNETOM Combi Suite Neurosurgery" Operator Manual—Combi Dockable Table (MAQUET), www.siemens.com/healthcare, 2015.

"MAGNETOM Combi Suite Neurosurgery", Operator Manual—Combi Dockable Table (Trumpf Medical), www.siemens.com/healthcare, 2015.

German Office action for related German Application No. 10 2014 225 519.8, dated Nov. 18, 2015, with English Translation.

* cited by examiner

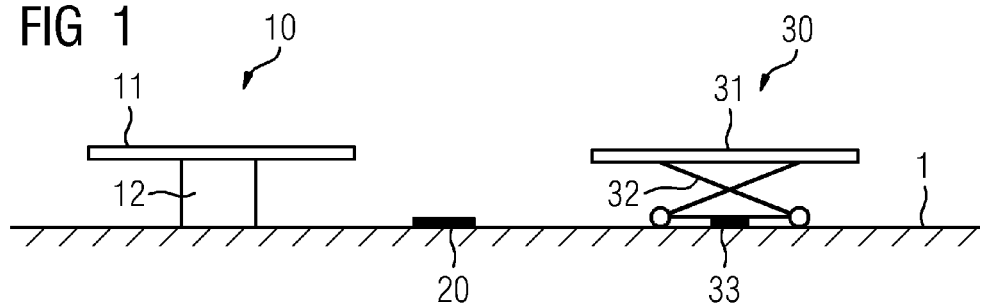
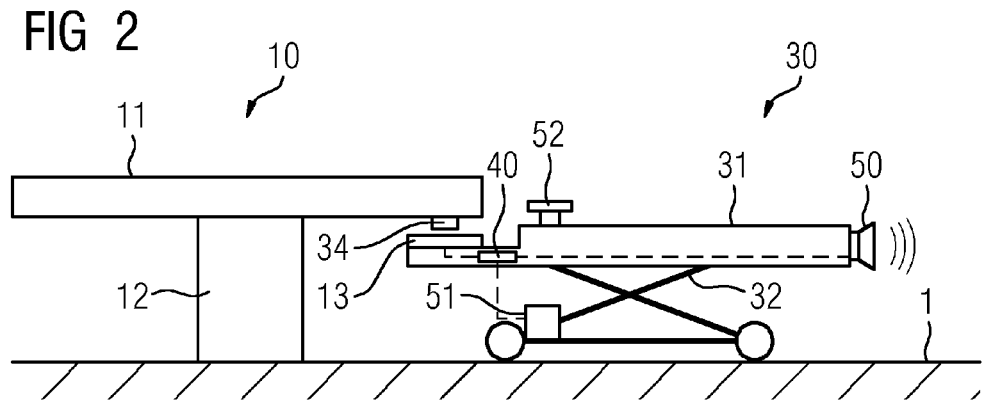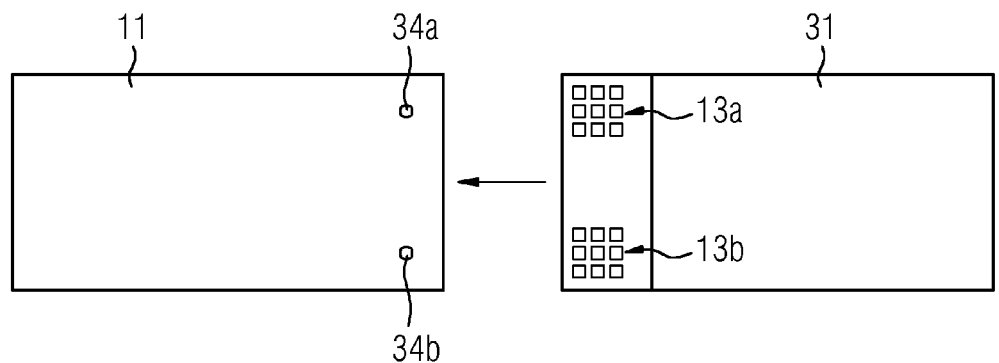

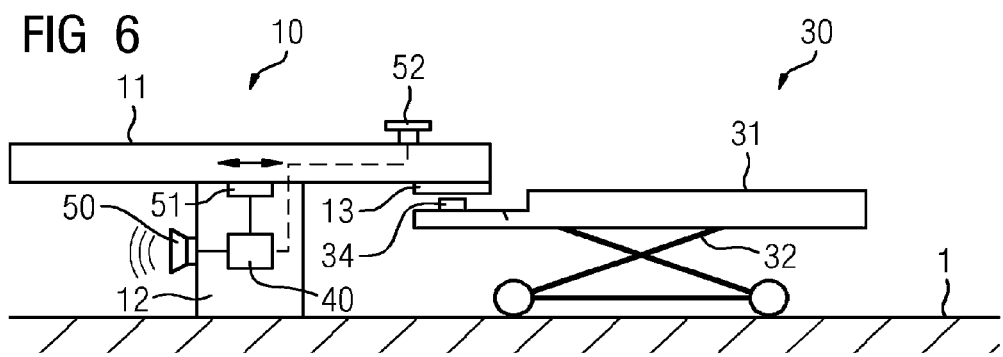
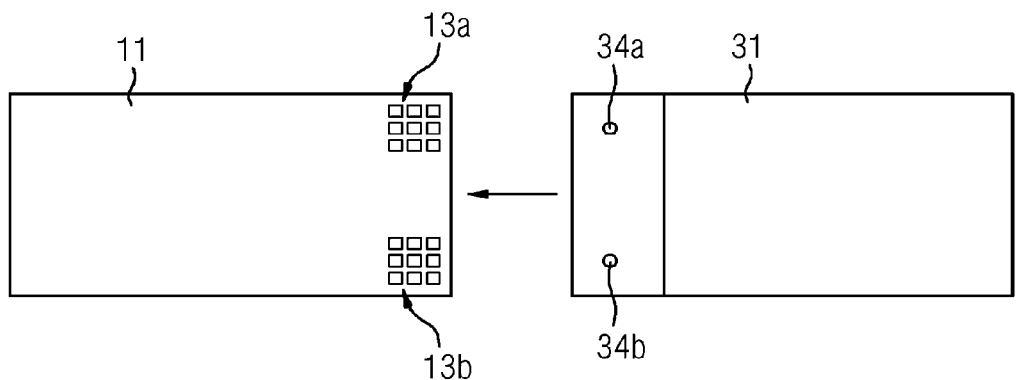

DEVICE AND METHOD FOR ASSISTING THE ALIGNING OF A DOCKABLE PATIENT SUPPORT

RELATED CASE

This application claims the benefit of DE 102014225519.8, filed on Dec. 11, 2014, which is hereby incorporated by reference in its entirety.

FIELD

The present embodiments relate to a device and method for assisting the aligning of a patient support which is dockable onto an operating table.

BACKGROUND

During medical treatment, it may be necessary for the patient to be transferred from a movable patient support to an operating table and/or from the operating table to a movable patient support. It can become necessary, for example, during or following a medical intervention on an operating table for a transfer to a patient support in order to carry out an imaging procedure, particularly by a magnetic resonance tomograph, to monitor the intervention.

In order to carry out this transfer process safely, the operating table is typically first docked onto the patient support. The patient support and the operating table are brought into a particular relative position.

FIG. 1 shows how the transfer of the patient who is initially situated, for example, on support surface 31 of the patient support 30, to the operating table 10 is carried out in the conventional manner according to the prior art. The support surface 11 of the operating table is connected by a locally fixed stationary column 12 to the floor 1. Beside the operating table situated on the floor 1 is a fixed floor dock 20. The patient support 30 is moved to the operating table 10 by a displacement unit 32 and locked in place there with the aid of the floor dock 20. This takes place with the aid of a locking device 33 mounted on the patient support 30. The locking device 33 is positioned such that the patient support 30 is correctly oriented relative to the operating table 10 following the locking procedure, so that the patient support may be docked to the operating table and a safe transfer of the patient may take place.

SUMMARY AND DESCRIPTION

The scope of the present invention is defined solely by the appended claims and is not affected to any degree by the statements within this summary.

With the present embodiments, the aligning of the patient support to the operating table is carried out with an alternative solution to the floor dock.

Accordingly, the device according to one embodiment includes a sensing unit, which may be arranged on the operating table and is configured to sense a feature of the patient support and/or of the operating table. The sensing unit senses said feature lying opposite the sensing unit by a position-dependent physical interaction and here from generates a signal, which depends on the relative spatial position between the patient support and the operating table. Furthermore, the device according to the embodiment includes an evaluating unit configured to receive the signal from the sensing unit and to generate an output that characterizes the relative position between the operating table and the patient support.

The device may be arranged solely on the components to be docked, particularly on a patient support and/or an operating table, so that further external spatially separate components, in particular a floor dock, may be omitted. The omission of additional components increases the flexibility of the workflow, particularly when, as with the floor dock, said components are installed spatially fixed. In addition, the omission of the floor dock creates better hygiene conditions. Furthermore, one embodiment offers the advantage that the device described herein is also usable with mobile operating tables, so that the operating table need not stand in a fixed position in a room.

The expression "operating table" is intended to denote an apparatus on which a patient may be positioned during a therapeutic medical treatment. The patient may herein be either a human or an animal. Said treatment does not necessarily have to be an operation in the narrow sense of the word, that is, a surgical intervention using instruments on or in the body of a patient. For example, a radiological intervention may be carried out on an operating table. Furthermore, the operating table does not necessarily have to be located in an operating theater, that is, a special room in a hospital or a medical practice in which operations, in the narrow sense, are carried out.

A patient support may serve, for example, as a positioning device for the patient during magnetic resonance tomography or another diagnostic imaging procedure. The patient support may also be used in the context of other medical treatments. Furthermore, the patient support also serves as a transport for transporting a patient from one room to another room or from a first medical device to a second medical device.

The sensing unit may be arranged on the patient support or on the operating table. It follows therefrom that the sensing unit does not necessarily need to be permanently fixed to the patient support or to the operating table. For example, the sensing unit may naturally also be subsequently mounted on an existing patient support and/or an existing operating table, particularly detachably. It is also conceivable that the user keeps just one sensing unit available that may be mounted on different patient supports as needed.

The sensing unit may be arranged on the patient support and/or on the operating table. For example, the sensing unit may be arranged on the patient support, wherein the sensing unit detects a feature of the operating table. The sensing unit may also be arranged on the operating table, wherein the sensing unit detects a feature of the patient support. It is also conceivable for the sensing unit to be arranged partially on the patient support and partially on the operating table, wherein the sensing unit detects a feature of the patient support and/or of the operating table.

The feature that is detected by the sensing unit may be of various kinds. Different possibilities are described below, although the invention is not restricted to these possibilities:
  Light signals, which represent the outline and/or the form of the operating table or the patient support. If the shape of the operating table or the patient support is known and the position of the sensing unit is known, the relative position between the operating table and the patient support may be calculated.
  Light signals, which are emitted by at least one light source mounted on the operating table or on the patient support.

Ultrasonic signals, which are emitted by at least one ultrasonic transducer mounted on the operating table or on the patient support, in particular, the amplitude and the propagation time of the ultrasonic signal.

Inductive signals, which are caused by at least one alternating field coil mounted on the operating table or on the patient support.

Mechanical resistances due to the shape of the operating table or the patient support, which may be detected by mechanical sensors.

The embodiment of the sensing unit depends on the type of physical interaction that is evoked by the feature to be sensed. For example, light signals may be received with photodetectors and ultrasonic signals with ultrasonic sensors. Advantageously, the sensing unit is adapted to the type of signal. For example, a modulation of the light signal may serve to differentiate the light signal from the ambient light. In this case, the sensing unit is able to receive modulated light signals and to pass the light signals on to the evaluating unit.

Typically, the physical interaction acts in a particular spatial direction, for example, the propagation direction of a light beam in the case of an optical interaction. The sensing unit, for example, an ultrasonic sensor for an acoustic interaction, typically has a sensing direction or an effective field with a particular directional characteristic. The effective directions of features to be sensed and the sensing unit may be matched to one another so that they are equally directed or so that the effective fields overlap. This may possibly be achieved in that the sensing unit is arranged suitably spatially oriented.

In the described embodiments of the device, it is conceivable that the effective direction of the physical interaction is oriented arbitrarily, in particular, horizontally and/or vertically. If the sensing unit includes a plurality of elements, the respective elements may also have different effective directions, for example, element 1 in a horizontal direction and element 2 in a vertical direction.

On the basis, firstly, of a possibly pre-determined embodiment of the patient support and/or the operating table and, secondly, the embodiment of the feature and the sensing unit, different preferred effective directions may result. If, for example, the patient support and the operating table have vertical end surfaces on which, particularly simply, a sensor and/or a light source may be mounted, then an effective direction perpendicularly thereto, that is, in the horizontal direction may be particularly advantageous. A similar principle also applies, naturally, for horizontal surfaces for which a vertical effective direction may prove to be particularly suitable.

Furthermore, knowledge of the effective direction of the feature to be sensed and of the sensing unit may be used by the evaluating unit, for example, for calculating the relative position between the patient support and the operating table.

The evaluating unit may be configured, for example, so that, from the known position of the features on the operating table and/or on the patient support and also from the known position of the sensing unit on the operating table and/or on the patient support, the evaluating unit determines the relative position between the operating table and the patient support. The evaluating unit generates an output depending on the relative position determined. This output may be variously configured. In particular, the receiver of this output, that is, the components, which further process this output, may differ.

In an advantageous embodiment, the output of the evaluating unit is a feedback signal, which may be perceived by an operator, in particular a visually and/or acoustically perceptible feedback signal.

Thus, for example, on manual positioning of the patient support, an acoustic signal may be given, via a loudspeaker, to the operator moving the patient support on reaching the target position, indicating that the target position has been reached. Thereupon, the operator stops the displacement process.

The target position may be, for example, the position of the patient support which represents the starting point for a subsequent step of docking the patient support to the operating table. During this docking step, the patient support and/or the operating table may be moved toward one another. It is herein conceivable that this docking movement may take place in any desired direction, particularly horizontally and/or vertically. This movement direction for the aligning according to some embodiments of the patient support relative to the operating table may differ from the movement direction of the docking step. Following completion of this docking step, a relative position between the patient support and the operating table is reached from which the transfer of the patient from the patient support to the operating table and/or from the operating table to the patient support is to take place. Typically, this position is determined such that the transfer may take place as safely as possible. However, it is also conceivable for the transfer of the patient to take place directly from the target position, that is, an additional docking act may be omitted.

In a further advantageous embodiment, the device also includes a motorized displacement unit for moving the patient support. The motorized displacement unit may be arranged on the patient support and/or on the operating table, wherein the output of the evaluating unit is a control signal that controls the displacement unit such that a movement of the patient support to a target position takes place.

In contrast to the prior art, the present embodiment therefore enables, for example, a self-driving and/or drive assisted patient support to be integrated into the workflow. A patient support of this type may include, for example, one or more motors that may move the patient support in different directions and/or sets the orientation of the wheels so that when the patient support is moved forward by the operator, the patient support is moved in the direction of the target position. The energy supply may take place, for example, with the aid of one or more accumulators.

The integration of the motorized displacement unit into the operating table is advantageous since operating tables often already include motors able to position the operating table in different directions. These already present motors may be made use of according to some embodiments.

Advantageously, the device is configured so that the sensing of the relative positioning within a sensing field takes place so that the direction in which the patient support and/or the operating table are moved in order to approach the target position is determined. Advantageously, this sensing field is dimensioned so that following a rough manual pre-positioning, a fine alignment takes place automatically by the motorized displacement unit. On reaching the target position, the displacement unit may then stop. If the motorized displacement unit is arranged on the patient support, the displacement unit typically includes at least one wheel connected to at least one motor, which is controlled with the aid of the evaluating unit.

In a further advantageous embodiment, the positioning takes place partially automatically. In this regard, the patient support, which often has a rectangular support surface, is displaced manually by the operator in the direction of the operating table, which often has a rectangular support surface, so that the respective shorter sides of the support surfaces are aligned parallel and the manual displacement direction is parallel to the longer sides of the support surfaces. Advantageously, the device is configured so that the sensing of the relative positioning within a sensing field takes place so that the direction in which the patient support is moved in order to approach the target position is determined. The displacement unit typically includes a wheel connected to at least one motor controlled with the aid of the evaluating unit. The motors are advantageously controlled so that the motors set the wheel or the wheels such that further manual advancing by muscle power leads to the patient support being moved in the direction of the target position. On reaching the target position, the displacement unit may then stop. This stop procedure may, for example, be automated with the aid of a motor brake or may be manual in that the reaching of the target position is indicated to the operator by an acoustic signal.

An automated or partially automated displacement is advantageous since thereby, due to the reduction of human, and therefore error-prone, interventions in this process, the degree of collision-safety may be increased.

A further embodiment provides that, in addition to the motorized displacement unit, the device additionally includes a dead man's circuit connected to the motorized displacement unit such that activation of the dead man's circuit feeds a signal to the evaluating unit.

A dead man's circuit may test whether the operator is interacting with the dead man's circuit or is actively operating the dead man's circuit. Otherwise, the lack of interaction may be an indication that the operator is not present or is not capable of acting. As soon as the operator no longer interacts with the dead man's circuit, the dead man's circuit would trigger a signal, which stops the automatic movement of the displacement unit. The checking is carried out, for example, in that the operator must permanently actuate a button arranged on the patient support during the automated movement. On release of the button, the signal is triggered, so that the movement stops. It is thus intended to prevent the operator being harmed or injured during the automated movement.

A further embodiment provides that the sensing unit includes at least one optical sensor wherein the feature detected is a light signal emitted by a light source.

Thus, for example, information may be derived by the evaluating unit from a signal amplitude of a bundled light beam generated by a light source mounted on the operating table. The light beam is received by a photodetector mounted on the patient support. Provided the positioning and orientation of the photodetector and the light source are known, said information serves for determining the relative spatial position between the patient support and the operating table.

A further embodiment provides that the feature detected is a light signal emitted by a light source arranged on the patient support disposed opposite the sensing unit or on the operating table disposed opposite the sensing unit, wherein the sensing unit includes at least one detector matrix adapted to sensing the light signal.

This embodiment is advantageous inter alia in that a detector matrix within the sensing field of the matrix provides the direction in which the patient support must be displaced in order to reach the target position can be determined. If, for example, a plurality, for example, at least two detector matrices are used, the alignment in a plane may also be unambiguously determined.

A further embodiment provides that the device additionally includes at least one light source arranged on the patient support, wherein the sensing unit includes at least one detector matrix arranged on the patient support. In this regard, the detected feature is a light signal emitted by a light source arranged on the patient support and is reflected by a reflector arranged on the operating table. The detector matrix is adapted for sensing the light signal.

This embodiment is advantageous particularly since with this, the making of modifications to the operating table may possibly be omitted since it is entirely conceivable that an existing operating table already has characteristic reflectors. Thus, all the components of the device may be arranged on the patient support. A reflector for intensifying the reflection may be arranged on the operating table. In this way, operating tables may be particularly easily adapted.

Normally, a detector matrix is configured areally, that is, the elements of the matrix are arranged adjoining one another on a surface. If the embodiment used includes at least one detector matrix, it is conceivable that the matrix is arrangeable on a horizontal surface and/or on a vertical surface and/or on a diagonal surface. If the matrix is arranged on a horizontal surface, then an optional step of docking the patient support on the operating table preferably takes place by a relative movement between the operating table and the patient support in the vertical direction. If the detector matrix is arranged on a vertical surface, the docking preferably takes place by a relative movement between the operating table and the patient support in the horizontal direction.

The sensing unit may include at least one distance sensor in order to support the collision-free docking of the patient support to the operating table.

Depending on the possibly already pre-determined embodiment of the patient support and/or of the operating table, one or another variant may be advantageous and, for example, implementable with little effort.

A further embodiment provides that the physical interaction takes place optically, acoustically, electrically, magnetically and/or mechanically. In particular, herein techniques based on infrared radiation, X-ray radiation, laser or radar may also be used.

A further embodiment provides that the device according to one embodiment additionally includes a patient support. This means that the patient support is equipped with the sensing unit and with the evaluating unit. Depending on the embodiment, a motorized displacement unit may also be mounted.

A further embodiment provides that the device additionally includes a patient support that may be used in a magnetic resonance tomograph. In order to use a patient support in a magnetic resonance tomograph, said patient support is advantageously configured so that the patient support interacts as little as possible with the electromagnetic field generated by the magnetic resonance tomograph, in order that the quality of the imaging is essentially not influenced. This means, according to the present embodiment, that the patient support is equipped with the sensing unit and with the evaluating unit. Depending on the embodiment, a motorized displacement unit may also be mounted.

A further embodiment provides that the device additionally includes an operating table with a motorized displacement unit for moving the operating table. Herein, the output of the evaluating unit is a control signal that controls the displacement unit such that a movement of the patient support to a target position takes place.

The advantage of this embodiment lies primarily therein that a motorized displacement unit of the operating table possibly already existing as standard may be utilized.

In a further variant, the device additionally includes a dead man's circuit connected to the motorized displacement unit such that activation of the dead man's circuit feeds a signal to the evaluating unit. In this case, also, the dead man's circuit may contribute to increasing the operating safety.

Methods according to embodiments for assisting the aligning of a patient support dockable onto an operating table will now be described. The advantages thereof essentially correspond to the advantages of the device for assisting the aligning of a patient support dockable onto an operating table and which have been disclosed in detail above. Features, advantages or alternative embodiments mentioned herein may also be transferred similarly to the other claimed subject matter and vice versa.

A method according to one embodiment includes the following acts:
 a) positioning the patient support relative to the operating table,
 b) sensing the relative position between the patient support and the operating table,
 c) comparing of the determined relative position with a target position, and
 d) outputting a result produced by the comparison The positioning of the patient support is carried out, for example, manually in that the operator pushes the patient support toward the operating table such that the patient support is as close as possible to the target position, as judged by eye. Thereafter, the relative position between the patient support and the operating table is detected. The accuracy of the position information determined depends on the embodiment of the sensing unit. The position information may be, for example, binary, that is, only distinguishing between the states that the target position has been reached or has not been reached. The position information may, however, also quantitatively describe the deviation in space or in a plane of the determined relative position and the target position. From the comparison between the determined relative position and the target position, a result is determined that, for example, is conveyed to the operator and/or for example, is used for controlling a motor.

If the relative position determined does not match the target position, it is advantageous to repeat acts a) to d) until the target position is reached. In particular, this iteration loop may be carried out entirely automatically, for example, until the target position is reached, from which position a possible docking act of the patient support onto the operating table may preferably be carried out. In order to increase the operating safety, in addition, the iteration process may be controlled such that the process is continued only for as long as a dead man's switch is activated, for example, by pressing a dead man's handle.

In an advantageous embodiment, the method serves for imaging by magnetic resonance tomography during an operation. During this process, a magnetic resonance tomography procedure is carried out before the aligning of the patient support relative to the operating table, while the patient under investigation is positioned on the patient support. Following the alignment, a possible docking, a locking of the patient support, and the transfer of the patient from the patient support to the operating table take place.

It is advantageous that following the ending of the magnetic resonance tomography, the transfer of the patient to the operating table may take place as rapidly as possible so that the treatment taking place there may be carried out on the basis of the most up-to-date possible findings resulting from the magnetic resonance tomography. This is ensured by the simplicity of the method according to some embodiments.

The locking of the patient support is advantageous since in the locked state, the patient support may no longer move relative to the operating table. This enables a reliable transfer of the patient. The locking may be achieved, for example, by fixing wheels of the patient support.

BRIEF DESCRIPTION OF THE DRAWINGS

The embodiments will now be described by reference to the drawings. These are schematic principle sketches in which:

FIG. 1 is a representation of the prior art.

FIGS. 2 and 3 are side and plan views of an embodiment wherein two detector matrices are arranged horizontally on a patient support.

FIGS. 6 and 7 are side and plan views of an embodiment wherein two detector matrices are arranged horizontally on the operating table.

DETAILED DESCRIPTION

Figure 4:
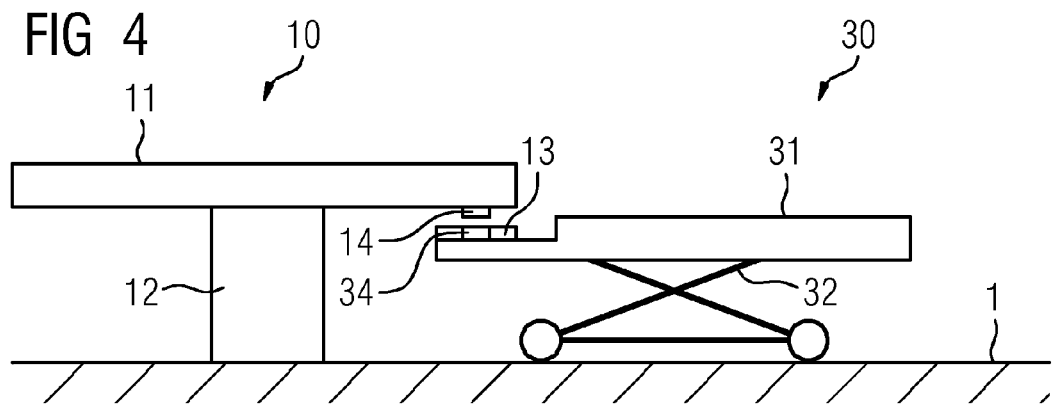
FIGS. 4 and 5 are side and plan views of a similar embodiment as shown in FIGS. 2 and 3 with two reflectors also being arranged on the operating table.

The accompanying diagrams, the technical details and the detailed description relate to a preferred embodiment of the invention, although this should not be construed as a restriction of the subject matter of the invention.

FIG. 2 is a side view and FIG. 3 is a plan view of an embodiment of a device for assisting the aligning of a patient support dockable onto an operating table. In FIG. 3, a support surface of the operating table is shown from below and a support surface of the patient support is shown from above.

The device includes a sensing unit 13 and an evaluating unit 40. The sensing unit 13 and the evaluating unit 40 are on the patient support 30.

The sensing unit 13 is arrangeable on the patient support 30 and/or on the operating table 10. In the example shown, the sensing unit 13 is arranged horizontally on an upper side of the support surface 31 of the patient support 30, for example consisting of two detector matrices 13a, 13b, for example CCDs. The sensing unit 13 is configured so that the sensing unit 13 may sense a feature of the opposite component, in the case shown the operating table 10, with the aid of a physical interaction, which depends on the position of the feature and therefrom may generate a signal that is also position-dependent.

The sensing unit 13 may include, for example, one or more optical sensors, wherein the feature detected may be a light signal emitted by a light source 34. In the example shown, the sensing is carried out by detection of light signals such as may be emitted by two light sources 34a, 34b mounted on the operating table 10 on the underside of the support surface 11. The surface areas of the support surfaces of the operating table 11 and the patient support 31 are parallel and are pushed one under the other during the positioning process. The detector matrices 13a, 13b on the patient support 30 and the light sources 34a, 34b on the operating table are spatially arranged and matched to one another such that, in the event that the patient support 30 is in the target position relative to the operating table 10, the light source 34a is aligned centrally to the detector matrix 13a and the light source 34b is aligned centrally to the detector matrix 13b. The light sources 34a, 34b herein emit their light perpendicularly to the surface area of the support surface 11 and thus impinge centrally upon the detector matrices 13a, 13b.

The physical interaction may take place, apart from the optical interaction represented in the figures, for example, acoustically, electrically, magnetically and/or mechanically.

The evaluating unit 40 may receive the signal generated by the sensing unit and generate an output therefrom that characterizes the relative position between the operating table and the patient support. In the example shown, the signals of the detector matrices 13a, 13b are read out, for example, pixel-wise, so that the evaluating unit 40 is thus able, within the sensing field essentially defined by the extent of the detector matrices 13a, 13b, to determine the position of the light beam on the surface of the detector matrices 13a, 13b. In this way, at the same time, the relative position between the patient support 30 and the operating table 10 may be determined.

In the example shown, the device also includes a displacement unit 32 including a motor 51 for moving the patient support. Using the information that the evaluating unit 40 has determined, a control signal for the motor 51 may be used for moving the patient support into the target position and may now be issued as the output.

Alternatively, for example, the orientation of the wheels may be set automatically by the evaluating unit so that, on manual pushing, movement into the target position takes place. On reaching the target position, an acoustic feedback signal that may be perceived by an operating person may be output, for example, with the aid of a loudspeaker 50. Alternatively, an optical feedback signal may be output. A dead man's circuit 52 may be connected to the motorized displacement unit such that activation of the dead man's circuit feeds a signal to the evaluating unit. A dead man's circuit, in particular, a safety cut-out circuit, may, for example, trigger a signal which stops the automatic movement of the displacement unit if, for example, a button placed on the patient support is not continuously pressed.

Once the target position has been reached, in a possible docking step, the patient support and the operating table may be brought into their final relative transfer position. In the examples shown in FIGS. 2 to 6, the docking movement D takes place in the vertical direction and in the example shown in FIG. 8, in the horizontal direction. However, embodiments are also conceivable in which the docking act takes place in any desired direction D.

Furthermore, the patient support 30 may be configured, for example, such that the patient support 30 may be used for positioning a patient in a medical imaging device, for example, a magnetic resonance tomograph during imaging.

FIGS. 4 to 9 are alternative embodiments to FIGS. 2 and 3 of a device for assisting the aligning of a patient support 30 dockable onto an operating table 10. The following description is essentially restricted to the differences from the exemplary embodiment in FIGS. 2 and 3 and, with regard to components, features and functions which remain the same, reference is made to the description of the exemplary embodiment in FIGS. 2 and 3. In principle, components, features and functions remaining the same are fundamentally identified with the same reference signs.

The device for assisting the aligning of a patient support 30 dockable onto an operating table 10 may also include one or more light sources 34 arranged on the patient support 30. The light sources 34 emit a light signal. Herein, the detector unit includes at least one detector matrix 13 arranged on the patient support 30 and may sense the light signal emitted as a feature. Herein, the light signal is reflected by at least one reflector 14 arranged on the operating table 10. Herein, the detector matrix 13 is adapted for sensing the light signal.

Figure 5:
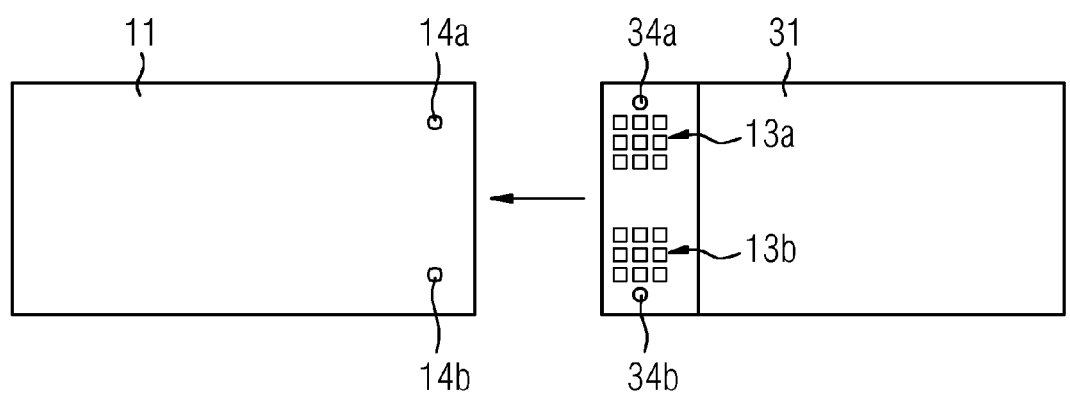

In the example shown in FIGS. 4 and 5, detector matrices 13a, 13b are mounted on the patient support 30 similarly to FIGS. 2 and 3. In addition, two reflectors 14a, 14b are attached to the operating table.

The detector matrices 13a, 13b and the light sources 34a, 34b on the patient support 31 and the reflectors 14a, 14b are each arranged such that, in the event that the patient support 30 is in the target position relative to the operating table 10, the reflection at the reflector 14a of the light beam emitted by the light source 34a meets the detector matrix 13a centrally and the reflection at the reflector 14b of the light beam emitted by the light source 34b meets the detector matrix 13a centrally. Alternatively, the system of light sources 34a, 34b, reflectors 14a, 14b and detector matrices 13a, 13b may be configured so that the light beams extend cross-wise, i.e. the light beam emerging from the light source 34a is reflected by the reflector 14a to the detector matrix 13b and the light beam emerging from the light source 34b is reflected by the reflector 14b to the detector matrix 13a. In both cases, either the reflector is tilted relative to the surface area of the support surface 11 or the light beam is tilted relative to the normal to the surface area of the support surface 31. Furthermore, the distance between the support surfaces 11 and 31 is constant.

Furthermore, the displacement device 32 may be configured so that the height of the support surface 31 is vertically changeable for vertical docking, in particular, such that the heights of the upper sides of the support surfaces of the operating table 11 and the patient support 31 may be brought into coincidence. In this way, a subsequent transfer process can be carried out particularly safely.

In FIGS. 6 and 7, a device is shown in which the feature to be sensed is a light beam emitted from each of two light sources 34a and 34b arranged on the upper side of the support surface 31 of the patient support 30. The light beam is received by each of two detector matrices 13a and 13b arranged on the underside of the support surface 11 of the operating table 10. These signals are passed on to the evaluating unit 40 arranged on the operating table 10 and are processed there. The output of the evaluating unit 40 is a control signal, which controls the automated displacement unit 51 such that a movement of the operating table to a target position takes place. Preferably, the device includes a dead man's circuit 52 connected via the evaluating unit 40 to the displacement unit 51.

This variant is particularly advantageous since, in order to move the operating table, a displacement unit 51 that possibly already exists as standard and is integrated into the operating table may be used.

Figure 8:
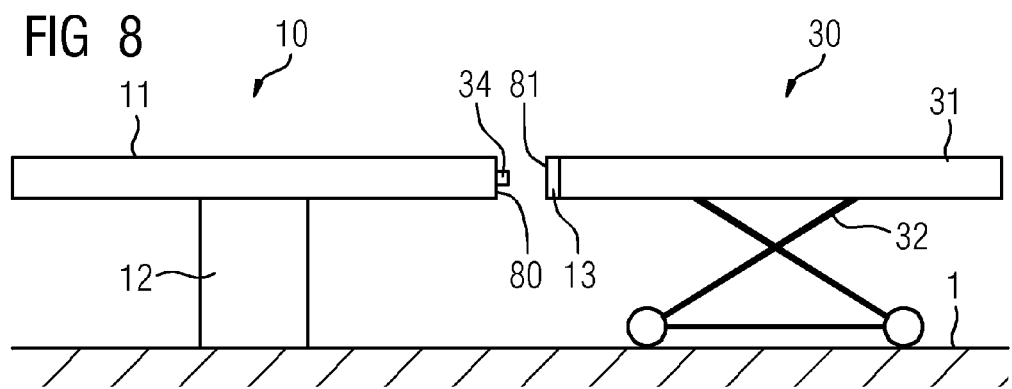
FIGS. 8 and 9 are side and plan view of an embodiment wherein two detector matrices are arranged vertically on the patient support.
Figure 9:
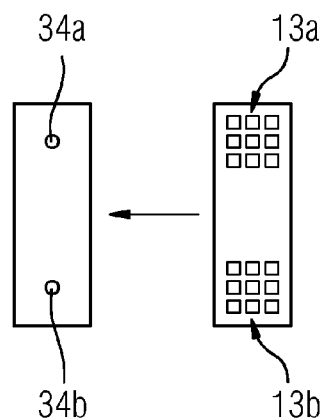

In FIGS. 8 and 9, a variant of the device according to one embodiment is shown in which the sensing unit 13 is not arranged, as in the preceding exemplary embodiments, horizontally on the underside and the upper side of the support surface 31, but rather vertically on an end side of the patient support 30. FIG. 9 shows the right end side surface 80 of the support surface 11 of the operating table 10 and the left end side surface 81 of the operating table 31 of the patient support 30. The feature to be sensed in the case shown is, respectively, a light beam emitted from each of two light sources 34a and 34b and received by two detector matrices 13a and 13b.

Optionally, the sensing unit 13 may be configured to generate a signal and to pass the signal on to the evaluating unit, from which the distance between the end side surfaces 80 and 81 are determinable, for example, by delay time measurement of an ultrasonic signal by a proximity sensor. This may facilitate collision-free docking of the patient support 30 onto the operating table 10.

Where applicable, it may also be advantageous to arrange the sensing unit in a diagonal plane. A diagonal plane should be understood as a plane the normal vector of which may be oriented arbitrarily in space.

Similarly to FIGS. 6 and 7, the sensing unit may naturally also be arranged vertically and/or diagonally on the operating table.

Figure 10:
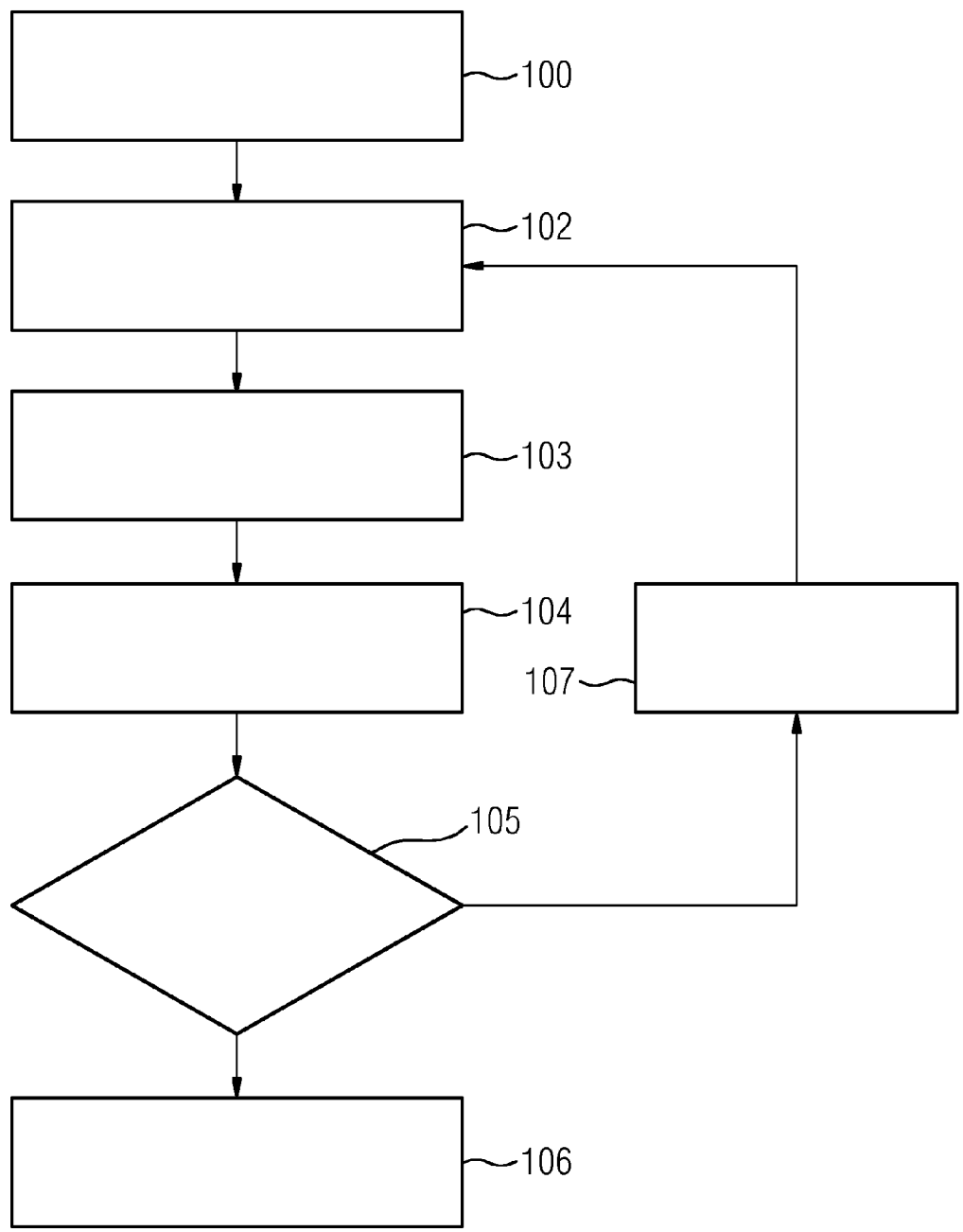
FIG. 10 is a flow diagram wherein, to reach a target position, the patient support is displaced.
Figure 11:
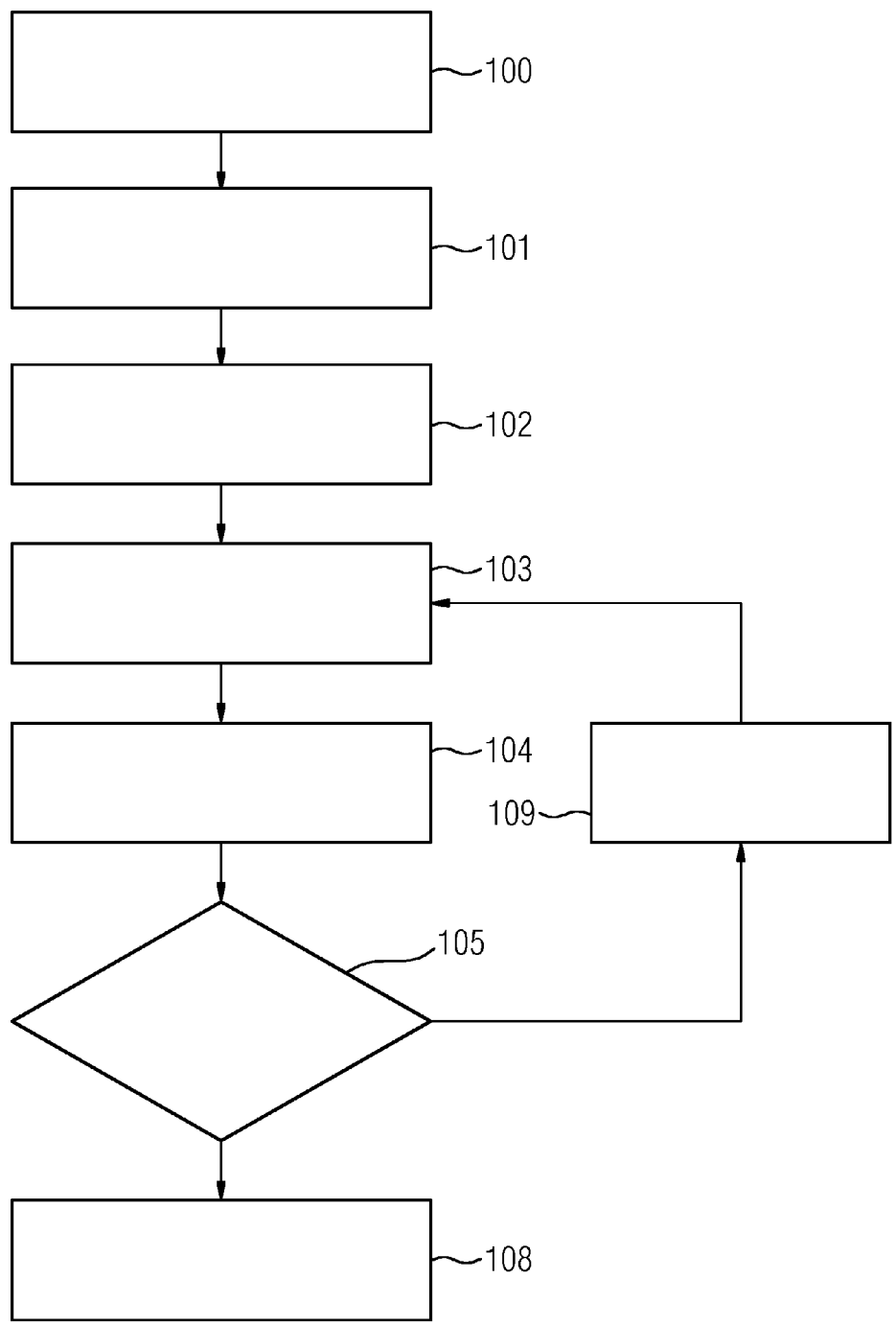
FIG. 11 is a flow diagram wherein to reach the target position, the operating table is displaced.

In FIGS. 10 and 11, by way of example, two alternative methods for aligning a patient support relative to an operating table are shown.

In FIG. 10 a diagram is shown which describes one possible sequence:
a) The patient support is pushed 100 under the operating table. This may take place, for example, manually by the operator and represents a relative positioning of the patient support to the operating table.
b) The relative position between the patient support and the operating table is detected 102 by a detector matrix.
c) A comparison is made 103 between the determined relative position and the target position.
d) The result of the comparison is output 104.
e) If the comparison 105 produces the result that the target position has been reached, following an optional docking step, the patient support is locked 106.

If the comparison 105 produces the result that the target position has not been reached, the patient support is displaced 107 and the acts from b) on are carried out iteratively. This iterative loop may take place entirely automatically with the aid of the apparatus shown in FIGS. 2, 3, 4, 5, 8 and 9. The displacement process may take place manually and/or automatically.

In FIG. 11 a further diagram is shown which describes one possible sequence:
a) The patient support is pushed under the operating table 100 and locked 101. This may take place, for example, manually by the operator and represents a relative positioning of the patient support to the operating table.
b) The relative position between the patient support and the operating table is detected 102 by a detector matrix.
c) A comparison is made 103 between the determined relative position and the target position.
d) The result of the comparison is output 104.
e) If the comparison 105 produces the result that the target position has been reached, following an optional docking act, the operating table is locked 108. If the sensing unit is horizontally arranged, the operating table may advantageously be lowered onto the patient support for docking.

If the comparison 105 produces the result that the target position has not been reached, the operating table is displaced 109 and the acts from b) on are carried out iteratively. The displacement process may take place manually and/or automatically, for example, assisted by a device as shown in FIG. 6.

Figure 12:
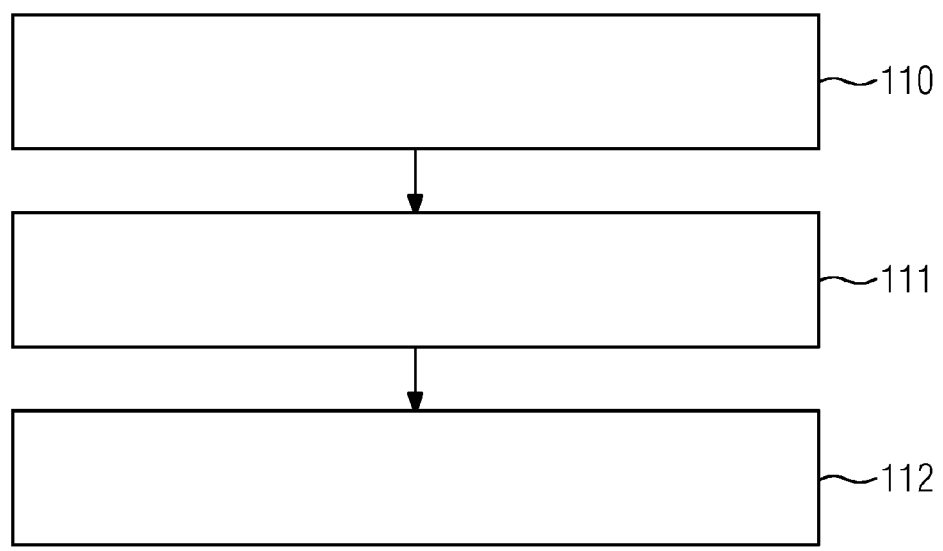
FIG. 12 is a flow diagram of a method that includes medical imaging, positioning of the patient support and a transfer procedure.

FIG. 12 shows, by way of example, a method for medical imaging during an operation. This method represents an extension of the method shown in FIGS. 10 and 11, with the following enhancements:

Before the positioning of the patient support relative to the operating table 111, a medical imaging process 110 is carried out, for example, with a magnetic resonance tomograph. Following the positioning of the patient support, the patient is transferred to an operating table 112.

Although the invention has been illustrated and described in detail based on the preferred exemplary embodiment, the invention is not restricted by the examples given and other variations can be derived therefrom by a person skilled in the art without departing from the protective scope of the invention.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A device for assisting the aligning of a moveable patient support dockable with an operating table, wherein the device comprises:
a sensor arranged on one of the moveable patient support or the operating table to sense a feature of the patient support and/or of the operating table, said feature lying opposite the sensor on another of the patient support or the operating table, the other different than the one, the sensor configured to sense a position-dependent physical interaction and to generate a signal that depends on a spatial relative position between the patient support and the operating table,
a light source arranged on the patient support, wherein the feature is a light signal emitted by the light source and reflected by at least one reflector arranged on the operating table; and
a controller configured to receive the signal from the sensor and to generate an output that characterizes the relative position between the operating table and the patient support.

2. The device as claimed in claim 1, wherein the output of the controller is a feedback signal to be perceived by an operator.

3. The device as claimed in claim 2 wherein the feedback signal comprises a visually and/or acoustically perceptible feedback signal.

4. The device as claimed in claim 1, further comprising a motorized displacement unit for moving the patient support, the motorized displacement unit arranged on the patient support, wherein the output of the controller is a control signal that controls the displacement unit such that a movement of the patient support to a target position takes place.

5. The device as claimed in claim 4, wherein the device additionally comprises a dead man's circuit connected to the motorized displacement unit such that activation of the dead man's circuit feeds a signal to the controller.

6. The device as claimed in claim 1, wherein the sensor comprises at least one optical sensor.

7. The device as claimed in claim 6, wherein the light source is arranged on the patient support disposed opposite the sensor or on the operating table disposed opposite the sensor, and wherein the sensor comprises at least one detector matrix configured to sense the light signal.

8. The device as claimed in claim 7, wherein the at least one detector matrix is arrangeable in a horizontal plane, a vertical plane, and/or in a diagonal plane.

9. The device as claimed in claim 6,
wherein the sensor comprises a detector matrix arranged on the patient support, the detector matrix is configured to detect the light signal.

10. The device as claimed in claim 1, wherein the physical interaction takes place optically, acoustically, electrically, magnetically, and/or mechanically.

11. A system comprising:
a patient support;
a sensor arranged on the patient support or an operating table and configured to sense a feature of the patient support and/or of the operating table, said feature lying opposite the sensor on another of the patient support or the operating table, the other different than the one, the sensor configured to sense a position-dependent physical interaction and to generate a signal that depends on the spatial relative position between the patient support and the operating table,
a light source arranged on the patient support, wherein the feature is a light signal emitted by the light source and reflected by at least one reflector arranged on the operating table; and
a controller configured to receive the signal from the sensor and to generate an output that characterizes the relative position between the operating table and the patient support.

12. The system of claim 11, wherein the patient support is configured such that the patient support is usable for positioning a patient in a medical imaging device during imaging.

13. The system of claim 11, further comprising a motorized displacement unit for moving the patient support, wherein the output of the controller is a control signal that controls the displacement unit such that a movement of the patient support to a target position takes place.

14. The system of claim 13, further comprising a dead man's circuit connected to the motorized displacement unit such that activation of the dead man's circuit feeds a signal to the controller.

15. A method for aligning a patient support relative to an operating table, the method comprising the acts:
a) positioning the patient support relative to the operating table;
b) detecting the relative position between the patient support and the operating table with a light source arranged on the patient support, wherein the relative position is detected based on a light signal emitted by the light source and reflected by at least one reflector arranged on the operating table;
c) comparing the determined relative position with a target position; and
d) outputting a result produced by the comparison.

16. The method as claimed in claim 15, wherein the acts a) to d) are used iteratively.

17. The method as claimed in claim 16, wherein the iterative acts take place automatically.

18. The method as claimed in claim 16, wherein the iterative acts are continued for as long as a dead man's circuit is activated.

19. A method for medical imaging during an operation, the method comprising the acts:
carrying out a medical imaging procedure during which the patient under investigation is positioned on the patient support;
aligning the patient support relative to an operating table with detection of a relative position between the patient support and the operating table, with comparison of the relative position with a target position, and with output of a result of the comparison, the detection being with a light source arranged on the patient support, wherein the relative position is detected based on a light signal emitted by the light source and reflected by at least one reflector arranged on the operating table;
locking the patient support in the target position; and
transferring the patient from the patient support to the operating table.

* * * * *